(12) United States Patent
Diehl et al.

(10) Patent No.: US 8,940,157 B2
(45) Date of Patent: Jan. 27, 2015

(54) PROCESS FOR THE HYDRODESULPHURIZATION OF A GASOLINE CUT IN THE PRESENCE OF A SUPPORTED SULPHIDE CATALYST PREPARED USING AT LEAST ONE CYCLIC OLIGOSACCHARIDE

(75) Inventors: Fabrice Diehl, Lyons (FR); Elodie Devers, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 184 days.

(21) Appl. No.: 13/812,711

(22) PCT Filed: Jun. 24, 2011

(86) PCT No.: PCT/FR2011/000366
§ 371 (c)(1),
(2), (4) Date: Mar. 15, 2013

(87) PCT Pub. No.: WO2012/022848
PCT Pub. Date: Feb. 23, 2012

(65) Prior Publication Data
US 2013/0168292 A1  Jul. 4, 2013

(30) Foreign Application Priority Data
Jul. 29, 2010 (FR) ...................................... 10 03191

(51) Int. Cl.
| | | |
|---|---|---|
| C10G 47/02 | (2006.01) | |
| C10G 45/08 | (2006.01) | |
| B01J 23/85 | (2006.01) | |
| B01J 27/185 | (2006.01) | |
| B01J 27/19 | (2006.01) | |
| B01J 31/02 | (2006.01) | |
| B01J 31/22 | (2006.01) | |
| B01J 37/02 | (2006.01) | |
| C07C 1/32 | (2006.01) | |
| C10G 45/10 | (2006.01) | |

(52) U.S. Cl.
CPC ................. *C10G 45/08* (2013.01); *B01J 23/85* (2013.01); *B01J 27/1853* (2013.01); *B01J 27/1856* (2013.01); *B01J 27/19* (2013.01); *B01J 31/0201* (2013.01); *B01J 31/2208* (2013.01); *B01J 37/0203* (2013.01); *C07C 1/321* (2013.01); *C10G 45/10* (2013.01); *C10G 2300/4018* (2013.01); *C10G 2300/104* (2013.01); *C10G 2300/1044* (2013.01); *C10G 2300/202* (2013.01); *C10G 2300/301* (2013.01)
USPC ........... 208/215; 502/305; 502/313; 502/315; 502/321; 502/325; 585/326

(58) Field of Classification Search
USPC .................. 502/313, 315, 321, 305, 325–326
See application file for complete search history.

(56) References Cited

U.S. PATENT DOCUMENTS

| 6,280,610 B1 | 8/2001 | Uragami et al. | |
| 2010/0012554 A1 | 1/2010 | Bai et al. | |
| 2012/0093703 A1* | 4/2012 | Lewis et al. | 423/213.2 |

FOREIGN PATENT DOCUMENTS

| WO | 96/41848 A1 | 12/1996 |
| WO | 2007/084438 A2 | 7/2007 |

OTHER PUBLICATIONS

International Search Report of International Application No. PCT/FR2011/000366 (Jan. 11, 2012).
A. Caro et al., "Enhancement of Dibenzothiophene Biodesulfurization Using B-Cyclodextrins in Oil-to-Water Media", Fuel, vol. 86, No. 16 (2007) pp. 2632-2636.

* cited by examiner

*Primary Examiner* — Brian McCaig
(74) *Attorney, Agent, or Firm* — Millen, White, Zelano & Branigan, P.C.

(57) ABSTRACT

Hydrodesulphurization of a gasoline cut containing hydrocarbons containing at least 2 carbon atoms per molecule and having an end point of 250° C. or less, by contacting the gasoline cut with at least one catalyst having an active phase of at least one metal from group VIII and at least one metal from group VIB deposited on a support, said catalyst being prepared using a process of:
i) contacting support with precursors of group VIII and group VIB metals;
ii) contacting support with at least one organic compound formed from at least one cyclic oligosaccharide composed of at least 6α-(1,4)-bonded glucopyranose subunits;
iii) drying to obtain at least said metal from group VIII and at least said metal from group VIB in the oxide form; then
iv) sulphurization such that said active phase is in the sulphide form;
i) and ii) being carried out separately, in any order, or simultaneously.

14 Claims, No Drawings

US 8,940,157 B2

PROCESS FOR THE HYDRODESULPHURIZATION OF A GASOLINE CUT IN THE PRESENCE OF A SUPPORTED SULPHIDE CATALYST PREPARED USING AT LEAST ONE CYCLIC OLIGOSACCHARIDE

FIELD OF THE INVENTION

The present invention relates to the field of hydrotreatment of hydrocarbon feeds containing sulphur, preferably of the gasoline type and in particular of the catalytically cracked gasoline type. More precisely, it pertains to the hydrodesulphurization of gasoline cuts the sulphur content of which has to be reduced in order to upgrade said cuts in the gasoline pool while limiting the octane number loss.

PRIOR ART

The increasing severity of automobile pollution regulations in 2009 in the European Community is forcing refiners to reduce the sulphur content in gas oils and gasolines very substantially to a maximum of 10 parts per million (ppm) of sulphur in gas oils and gasolines from the 1 Jan. 2009, down from 50 ppm on 1 Jan. 2005 (measured using the ASTM D-4294 method). Such regulations not only concern the total quantity of sulphur, but also the nature of the sulphur-containing compounds, for example mercaptans. These constraints mean that new refining units are needed, or that the iso-volume activity of hydrotreatment catalysts must be substantially increased. Further, these new regulations are also accompanied by restrictions regarding the quality produced, for example for gasolines with a high octane number.

The production of reformulated gasolines, i.e. derived from hydrotreatment processes, satisfying new environmental regulations necessitates reducing their concentration in mono-olefins as much as possible in order to keep the octane number high, and also reducing their sulphur content. Catalytically cracked gasolines (FCC), which may represent 30% to 50% by volume of the gasoline pool, have high olefins and sulphur contents. Almost 90% of the sulphur present in reformulated gasolines can be attributed to catalytically cracked gasolines. Desulphurization (hydrodesulphurization) of gasolines, principally catalytically cracked gasolines (FCC), is thus clearly important in order to comply with the specifications. Hydrotreatment (or hydrodesulphurization) of catalytically cracked gasolines, when carried out under the conventional conditions known to the skilled person, can reduce the sulphur content of a cut. However, that process suffers from the major drawback of causing a very large drop in the octane number of the cut due to saturation of all of the olefins during the hydrotreatment. Thus, processes that can intensely desulphurize catalytically cracked gasolines while keeping the octane number to a high level, i.e. by keeping the selectivity high (ratio between hydrodesulphurization and hydrogenation of olefins) have been proposed. As an example, U.S. Pat. No. 5,318,690 proposes a process consisting of fractionating the gasoline, sweetening the light fraction and hydrotreating the heavy fraction on a conventional catalyst then treating it on a ZSM-5 zeolite to approximately recover the initial octane number.

In addition to selectivity, another catalytic performance which refiners want to improve is the catalytic activity. An effective means for increasing the activity of supported catalysts is to increase the quantity of active phase in the sulphide form, which initially results in maximized deposition of the active phase in the oxide form associated with the surface area of the support. However, this maximized quantity (normally deposited by dry impregnation) is limited by the textural properties of the support, in particular its specific surface area and its pore volume. Furthermore, in the particular case in which the support used comprises the element aluminium, this large concentration of deposited oxide phase favours the formation of crystalline oxide phases of the $Al_2(MoO_4)_3$, $CoAl_2O_4$ or $NiAl_2O_4$ type, etc, which prove to be refractory to the sulphurization step. This logically results in an indirect loss of catalytic activity since not all of the deposited oxide phase is used to its maximum potential. Furthermore, an increase in the active phase content may result in the formation of crystallites of $MoO_3$, $NiO$, $CoO$, $Co_3O_4$ or $CoMoO_4$, of a size sufficiently large to be detected in X ray diffraction. These species are also known to reduce the degree of sulphurization of hydrotreatment catalysts and thus their performances.

The composition and use of hydrotreatment catalysts and in particular of hydrodesulphurization catalysts have been described particularly well in the article by B S Clausen, H T Topsøe, F E Massoth in the publication "Catalysis Science and Technology", 1996, volume 11, Springer-Verlag. Thus, these catalysts generally comprise at least one metal from group VIB and/or at least one metal from group VIII of the periodic classification of the elements. The most common formulations are of the cobalt-molybdenum (CoMo), nickel-molybdenum (NiMo) and nickel-tungsten (NiW) type. These catalysts may be in the bulk or in the supported form. In this latter case, the porous matrix is generally an amorphous or low crystallinity oxide (alumina, silica-alumina, etc), optionally associated with a zeolitic or non-zeolitic molecular sieve. After preparation, said catalysts are usually in the oxide form. Their active and stable form for hydrotreatment processes, in particular for hydrodesulphurization processes, is the sulphurized form, and so these catalysts undergo a sulphurization step.

However, the dispersion of the active phase or of said oxide or oxyhydroxide precursors is directly linked to the specific surface area of the support: for high surface densities of molybdenum, the formation of phases which are refractory to sulphurization by sintering has been reported; in the case of CoMo catalysts, for example, these are the phases $CoMoO_4$ or $Co_3O_4$ (B S Clausen, H T Topsøe, F E Massoth in the publication "Catalysis Science and Technology", volume 11 (1996), Springer-Verlag). Novel techniques for preparing catalysts have to be developed in order to further improve the performances of such catalysts and comply with future legislation.

In particular, interactions between the support and the precursors for the active phase which result in species which are refractory to sulphurization (for example, $Al_2(MoO_4)_3$, $CoAl_2O_4$ or $NiAl_2O_4$, which are of no use to the catalytic reaction and which have undesirable effects on the catalytic activity, should be controlled.

Thus, any means aimed at limiting the formation of such phases, which are either refractory to sulphurization or induce immobilization of the species in a less catalytically active form, would be interesting in order to result in a significant improvement in the performances of hydrotreatment catalysts and in particular hydrodesulphurization catalysts. To this end, several lines of investigation have been followed. Of these, technological solutions that can modify the support-precursor interactions of the oxide phases look promising. As an example, patent application WO 2007/084438A2 shows that using complexing agents such as nitrilotriacetic acid (NTA) or ethylenediamine tetraacetic acid (EDTA) can be used to produce hydrotreatment catalysts, in particular catalysts for the hydrodesulphurization of gasolines supported on silica with very good selectivity as regards the desulphurization of catalytically cracked gasolines (FCC), limiting the saturation of olefins thereby. It has also been recommended, in patent application EP-A-0 601 722, that an oil hydrotreatment catalyst prepared in the presence of an additive agent selected from di-alcohols or tri-alcohols containing 2 to 10 carbon atoms per molecule, the ethers of said alcohols, monosaccharides or disaccharides be used. Adding that type of additive can improve the activity of the hydrotreatment catalysts.

SUMMARY AND ADVANTAGE OF THE INVENTION

The present invention concerns a process for the hydrodesulphurization of a gasoline cut containing hydrocarbons containing at least 2 carbon atoms per molecule and having an end point of 250° C. or less, said process consisting of bringing said gasoline cut into contact with at least one catalyst the active phase of which comprises at least one metal from group VIII and at least one metal from group VIB deposited on a support formed from at least one oxide, said catalyst being prepared using a process comprising at least:
i) at least one step for bringing at least said support into contact with at least one solution containing at least one precursor of at least said metal from group VIII and at least one precursor of at least said metal from group VIB;
ii) at least one step for bringing at least said support into contact with at least one organic compound formed from at least one cyclic oligosaccharide composed of at least 6α-(1,4)-bonded glucopyranose subunits;
iii) at least one drying step to obtain at least said metal from group VIII and at least said metal from group VIB in the oxide form; then
iv) at least one sulphurization step such that said active phase is in the sulphide form;
the steps i) and ii) possibly being carried out separately, in any order, or simultaneously.

In accordance with the hydrodesulphurization process of the invention, said metal from group VIII present in the active phase of the catalyst is preferably cobalt and said metal from group VIB present in the active phase is preferably molybdenum. In accordance with the hydrodesulphurization process of the invention, said catalyst is preferably prepared in the presence of a cyclodextrin as the organic compound.

Surprisingly, it has been discovered that a sulphide catalyst the active phase of which comprises at least one metal from group VIII, preferably a non-noble metal from group VIII, and at least one metal from group VIB prepared in the presence of at least one organic compound formed from at least one cyclic oligosaccharide composed of at least 6α-(1,4)-bonded glucopyranose subunits, preferably a cyclodextrin, when used in a process for hydrodesulphurization of a gasoline cut, has improved catalytic performances, especially in terms of catalytic activity and/or in terms of selectivity. In particular, this results in enhanced reduction of the sulphur content of the gasoline cut obtained at the end of said hydrodesulphurization process, especially when the support for the catalyst is based on alumina, and/or the production of a gasoline cut with a very low octane number loss, especially when the support is silica-based.

DESCRIPTION OF THE INVENTION

The present invention concerns a process for the hydrodesulphurization of a gasoline cut containing hydrocarbons containing at least 2 carbon atoms per molecule and having an end point of 250° C. or less, said process consisting of bringing said gasoline cut into contact with at least one catalyst the active phase of which comprises at least one metal from group VIII and at least one metal from group VIB deposited on a support formed from at least one oxide, said catalyst being prepared using a process comprising at least:
i) at least one step for bringing at least said support into contact with at least one solution containing at least one precursor of at least said metal from group VIII and at least one precursor of at least said metal from group VIB;
ii) at least one step for bringing at least said support into contact with at least one organic compound formed from at least one cyclic oligosaccharide composed of at least 6α-(1,4)-bonded glucopyranose subunits;
iii) at least one drying step to obtain at least said metal from group VIII and at least said metal from group VIB in the oxide form; then
iv) at least one sulphurization step such that said active phase is in the sulphide form;
the steps i) and ii) possibly being carried out separately, in any order, or simultaneously.

Said gasoline cut treated in the hydrodesulphurization process of the invention is a gasoline cut containing sulphur and olefinic hydrocarbons. It contains hydrocarbons, in particular olefinic hydrocarbons, containing at least 2 carbon atoms per molecule, preferably at least 5 carbon atoms per molecule, and with an end point or 250° C. or less. Said gasoline cut preferably contains hydrocarbons, in particular olefinic hydrocarbons, containing 5 to 8 carbon atoms per molecule. Said cut is preferably derived from a coking unit, a visbreaking unit, a steam cracking unit or from a fluid catalytic cracking (FCC) unit. Advantageously, said gasoline cut may optionally be composed of a significant fraction of gasoline deriving from other production processes such as atmospheric distillation (straight run gasoline) or gasoline from conversion processes (coking or steam cracking gasoline). Said gasoline cut has a sulphur content in the range 200 to 5000 ppm by weight, preferably in the range 500 to 2000 ppm by weight. Highly preferably, said gasoline cut is a cut derived from a fluid catalytic cracking unit. Such a gasoline cut from a catalytic cracking unit, advantageously treated in the hydrodesulphurization process of the invention, contains approximately 20% to 40% by weight of olefinic compounds such as 2,3-dimethyl-but-1-ene, 4,4-dimethylcyclopentene, 2-methyl-2-heptene, hex-1-ene, 30% to 60% by weight of aromatic compounds such as ethylbenzene or ortho-xylene, and 20% to 50% by weight of saturated paraffin or naphthene type compounds such as 2-methylhexane or 1-methylcyclopentane. Of the olefinic compounds, branched olefins, in particular 3-methyl-cis-pent-2-ene or 3-methyl-cis-hex-3-ene, are in the majority compared with straight chain and cyclic olefins such as hex-1-ene, hept-1-ene or cyclopentene. Said gasoline cut derived from a catalytic cracking unit advantageously treated in the hydrodesulphurization process of the invention may contain a small quantity, i.e. not exceeding 5% by weight, of the gasoline cut, of polyunsaturated compounds of the diolefinic or acetylenic type, the presence of said polyunsaturated compounds preferably being in the range 100 ppm to 5% by weight, highly preferably in the range 100 ppm to 2% by weight. Said gasoline cut derived from a catalytic cracking unit preferably has a sulphur content in the range 200 to 5000 ppm by weight, preferably in the range 500 to 2000 ppm by weight.

In particular, the sulphur-containing compounds present in the gasoline cut to be treated in accordance with the hydrodesulphurization process of the invention, in particular present in the gasoline cut from a catalytic cracking unit, are thiophenic compounds such as 3-methylthiophene or 3,4-dimethylthiophene and benzothiophenic compounds such as benzothiophene, mercaptans (non-cyclic sulphur-containing compounds having a S—H bond), for example propanethiol, only being present in small quantities, i.e. in a quantity by weight which is advantageously in the range 10 to 100 ppm.

The hydrodesulphurization process of the invention is intended to improve the conversion of the sulphur-containing compounds present in the gasoline cut by an increased catalytic activity of the catalyst in order to reduce the sulphur content in the gasoline cut intended to be integrated into the gasoline pool and/or to improve the selectivity of said catalyst in order to limit hydrogenation of mono-olefinic compounds and aromatic compounds having a high octane number into saturated compounds with a lower octane number. Depending on the composition of the catalyst employed, the hydrodesulphurization process of the invention can improve the catalytic activity without degradation of the selectivity or improve the selectivity without degradation of the catalytic activity.

The technology of the hydrodesulphurization process of the invention involves, for example, injecting the gasoline cut and hydrogen into at least one fixed bed, moving bed or ebullated bed reactor, preferably into a fixed bed reactor.

The hydrodesulphurization process of the invention is carried out in the gas phase. It is carried out under the following operating conditions: a temperature in the range 200° C. to 400° C., preferably in the range 250° C. to 350° C., a total pressure in the range 1 to 3.5 MPa, more preferably in the range 1 MPa to 2.5 MPa, with a ratio of the volume of hydrogen to the volume of gasoline cut in the range 100 to 600 liters per liter and more preferably in the range 200 to 400 liters per liter. Finally, the hourly space velocity (HSV) is the inverse of the contact time expressed in hours. It is defined by the ratio of the volume flow rate of the liquid gasoline cut to the volume of catalyst loaded into the reactor. It is generally in the range 1 to 10 $h^{-1}$, preferably in the range 2 to 8 $h^{-1}$.

The catalyst employed to carry out the hydrodesulphurization process of the invention comprises an active metallic phase deposited on a support, said active phase comprising at least one metal from group VIII of the periodic classification of the elements and at least one metal from group VIB of the periodic classification of the elements. Preferably, the active phase of said catalyst further comprises phosphorus.

In general, the quantity of metal(s) from group VIB in said oxide catalyst from said step iii) is in the range 1% to 20% by weight of oxide(s) of metal(s) from group VIB, preferably in the range 1.5% to 18% by weight of oxide(s) of metal(s) from group VIB, highly preferably in the range 2.5% to 18% by weight of oxide(s) of metal(s) from group VIB. Preferably, the metal from group VIB is molybdenum or tungsten or a mixture of these two elements; more preferably, the metal from group VIB is constituted solely by molybdenum or tungsten. Highly preferably, the metal from group VIB is molybdenum.

In general, the quantity of metal(s) from group VIII in said oxide catalyst from said step iii) is in the range 0.1% to 20% by weight of oxide(s) of metal(s) from group VIII, preferably in the range 0.2% to 10% by weight of oxide(s) of metal(s) from group VIII, highly preferably in the range 0.3% to 5% by weight of oxide(s) of metal(s) from group VIII. Preferably, the metal from group VIII is a non-noble metal from group VIII of the periodic classification of the elements. Highly preferably, said metal from group VIII is cobalt or nickel or a mixture of these two elements; more preferably, the metal from group VIII is constituted solely by cobalt or nickel. Highly preferably, the metal from group VIII is cobalt.

The molar ratio of metal(s) from group VIII to metal(s) from group VIB in the oxide catalyst derived from said step iii) is preferably in the range 0.1 to 0.8, highly preferably in the range 0.2 to 0.6, and still more preferably in the range 0.3 to 0.5.

When the catalyst contains phosphorus, the quantity of phosphorus in said oxide catalyst from said step iii) is preferably in the range 0.1% to 10% by weight of $P_2O_5$, more preferably in the range 0.2% to 5% by weight of $P_2O_5$, highly preferably in the range 0.3% to 4% by weight of $P_2O_5$, and still more preferably in the range 0.35% to 3% by weight of $P_2O_5$.

The molar ratio of phosphorus to metal(s) from group VIB in the oxide catalyst derived from said step iii) is 0.25 or more, preferably 0.27 or more, more preferably in the range 0.27 to 2.00, and still more preferably in the range 0.35 to 1.40.

The support on which the active phase is deposited is advantageously formed from at least one porous solid in the oxide form selected from the group constituted by aluminas, silicas, silica-aluminas or from oxides of titanium or magnesium used alone or as a mixture with alumina or silica-alumina. It is preferably selected from the group constituted by silicas, transition aluminas and silica-aluminas. Highly preferably, the support is essentially constituted by a transition alumina or silica. A "support essentially constituted by a transition alumina" comprises at least 51% by weight, preferably at least 60% by weight and highly preferably at least 80% by weight or even at least 90% by weight of said transition alumina. The term "transition alumina" means, for example, an alpha phase alumina, a delta phase alumina, a gamma phase alumina or a mixture of these various phases of alumina. A "support essentially constituted by silica" comprises at least 51% by weight, preferably at least 60% by weight, highly preferably at least 80% by weight or even at least 90% by weight of silica. In a first, highly preferred implementation, said support is constituted solely by a transition alumina. In accordance with a second highly preferred implementation, said support is constituted solely by silica. The pore volume of the support is generally in the range 0.4 to 1.4 $cm^3/g$ and preferably in the range 0.5 to 1.3 $cm^3/g$. The specific surface area of the support is generally in the range 40 to 300 $m^2/g$, preferably in the range 60 to 250 $m^2/g$. Said porous support is advantageously in the form of beads, extrudates, pellets or irregular, non-spherical agglomerates the specific form of which may be the result of a crushing step. Highly advantageously, said support is in the form of beads or extrudates.

The catalyst employed in the hydrodesulphurization process of the invention is prepared using a process comprising at least:

i) at least one step for bringing at least said support into contact with at least one solution containing at least one precursor of at least said metal from group VIII and at least one precursor of at least said metal from group VIB;

ii) at least one step for bringing at least said support into contact with at least one organic compound formed from at least one cyclic oligosaccharide composed of at least 6α-(1,4)-bonded glucopyranose subunits;

iii) at least one drying step to obtain at least said metal from said group VIII and at least said metal from group VIB in the oxide form; then iv) at least one sulphurization step such that said active phase is in the sulphide form;

the steps i) and ii) possibly being carried out separately, in any order, or simultaneously.

In accordance with the implementation of said step i), at least said metal from group VIII and at least said metal from group VIB may be deposited on said support using any method which is well known to the skilled person. Said step i) is preferably carried out by impregnation of the support with at least one solution containing at least one precursor of said metal from group VIII and at least one precursor of said metal from group VIB. In particular, said step i) may be carried out by dry impregnation, by excess impregnation or by deposition-precipitation using methods which are well known to the skilled person. Preferably, said step i) is carried out by dry impregnation, which consists of bringing the catalyst support into contact with a solution containing at least one precursor of said metal from group VIII and at least one precursor of said metal from group VIB, wherein the volume is equal to the pore volume of the support to be impregnated. This solution contains the metallic precursors of the metal or metals from group VIII and of the metal or metals from group VIB in the desired concentration. Said solution may also contain hydrogen peroxide, especially in the case in which the metal from group VIII is cobalt and the metal from group VIB is molybdenum.

Said metal(s) from group VIII and said metal(s) from group VIB are brought into contact with said support using any metallic precursor which is soluble in an aqueous phase or in an organic phase. Preferably, said precursor(s) of the metal(s) from group VIII and said precursor(s) of the metal(s) from group VIB are introduced in aqueous solution. When the metal from group VIII is cobalt, cobalt nitrate, cobalt hydroxide or cobalt carbonate is advantageously used as the precursor. When the metal from group VIII is cobalt, cobalt nitrate, cobalt hydroxide or cobalt carbonate is advantageously used as the precursor. When the metal from group VIII is nickel, nickel nitrate, nickel hydroxide or nickel carbonate is advantageously used as the precursor. When said metal from group VIB is molybdenum, ammonium heptamoybdate or molybdenum oxide is advantageously used. When said metal from group VIB is tungsten, ammonium metatungstate is advantageously used. When phosphorus is present in the active phase of the catalyst, phosphoric acid is advantageously used as the precursor. Any other salt which is known to the skilled person with sufficient solubility in aqueous solution and which can be decomposed during a drying step, in particular during the drying step of said step iii), may also be used.

Contact of said organic compound used to carry out said step ii) with said support is carried out by impregnation, in particular by dry impregnation or excess impregnation, preferably by dry impregnation. Said organic compound is preferably impregnated onto said support after dissolving into aqueous solution. The impregnation solution advantageously comprises an acid, for example acetic acid.

Said organic compound is formed from at least one cyclic oligosaccharide composed of at least 6α-(1,4)-bonded glucopyranose subunits. A spatial representation of a glucopyranose subunit is given below:

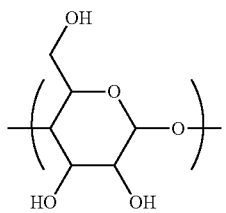

Said organic compound is preferably selected from cyclodextrins, substituted cyclodextrins, polymerized cyclodextrins and mixtures of cyclodextrins. Cyclodextrins are a family of cyclic oligosaccharides composed of α-(1,4)-bonded glucopyranose subunits. They are cage molecules. In accordance with the invention, preferred cyclodextrins are α-cyclodextrin, β-cyclodextrin and γ-cyclodextrin respectively composed of 6, 7 and 8α-(1,4)-bonded glucopyranose subunits. Developed representations of α-cyclodextrin, β-cyclodextrin and γ-cyclodextrin are given below. Preferably, to carry out said step ii), β-cyclodextrin is used, composed of 7α-(1,4)-bonded glucopyranose subunits. Cyclodextrins are commercially available compounds.

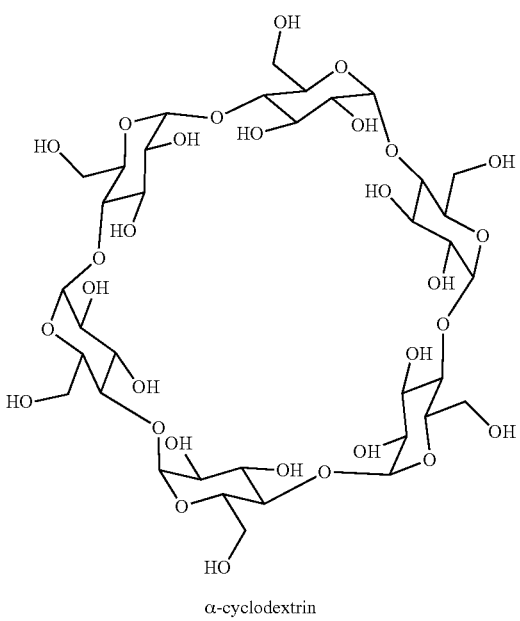

α-cyclodextrin

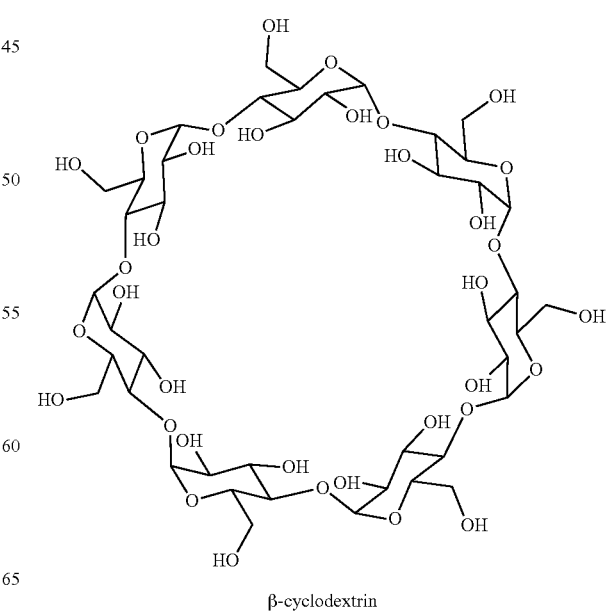

β-cyclodextrin

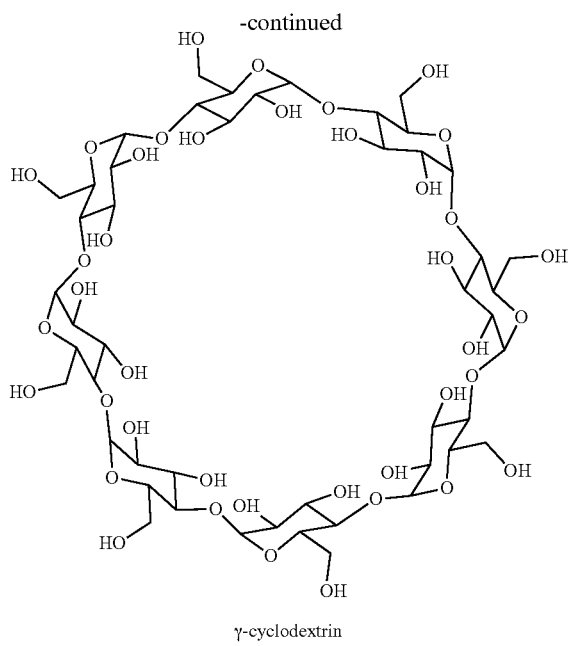

γ-cyclodextrin

The substituted cyclodextrins advantageously employed to carry out said step ii) are constituted by 6, 7 or 8α-(1,4)-bonded glucopyranose subunits, wherein at least one is mono- or polysubstituted. The substituents may be attached to one or more hydroxyl group(s) present in the molecule, namely to hydroxyl groups bonded directly to the cycle of a glucopyranose unit and/or to the hydroxyl bonded to the $CH_2$ group itself bonded to the cycle of a glucopyranose unit. More preferably, said substituted cyclodextrins carry one or more substituents, which may be identical or different, selected from saturated or unsaturated alkyl radicals, which may or may not be functionalized, and ester, carbonyl, carboxyl, carboxylate, phosphate, ether, polyether, urea, amide, amine, triazole or ammonium functions. Preferred substituted cyclodextrins are methylated, ethylated, propylated and allyl (i.e. having a function with the semi-developed formula —$CH_2$—CH=$CH_2$) cyclodextrins, succinylated (i.e. having a function with the semi-developed formula R—OCO—$CH_2$—$CH_2$COOH) cyclodextrins, carboxylated, carboxymethylated, acetylated, 2-hydroxypropylated and polyoxyethylenated cyclodextrins. The cyclodextrin mono- or poly-substituent groups may also be a monosaccharide or disaccharide molecule such as a molecule of maltose, glucose, fructose or saccharose.

Particularly advantageous substituted cyclodextrins for carrying out said step ii) are hydroxypropyl beta-cyclodextrin and methylated beta-cyclodextrins.

The polymerized cyclodextrins which are advantageously employed for carrying out said step ii) are polymers wherein the monomers are each constituted by a cyclic oligosaccharide composed of 6, 7 or 8α-(1,4)-bonded glucopyranose subunits, which may or may not be substituted. A cyclodextrin in the polymerized form, cross-linked or not, which may advantageously be used to carry out said step ii) is, for example, of the type obtained by polymerization of monomers of beta-cyclodextrin with epichlorhydrin or a polyacid.

Advantageous mixtures of cyclodextrins employed in carrying out said step ii) employ substituted or unsubstituted cyclodextrin. Said mixtures could, for example, contain each of the three types of cyclodextrins (alpha, beta and gamma) jointly and in varying proportions.

Introduction of said organic compound, preferably a cyclodextrin and highly preferably beta-cyclodextrin, for carrying out said step ii) is such that the molar ratio {(metal(s) from groups (VIII and VIB) in the oxide form present in the active phase of the catalyst obtained at the end of said step iii)/organic compound} is in the range 10 to 300, preferably in the range 25 to 180. The metals from groups VIII and VIB taken into account for the calculation of said molar ratio are the metals introduced to carry out said step i) and in the oxide form in the active phase of the catalyst obtained from said step iii). As a result, said metal(s) from group VIII and VIB may be in the sulphide form: they will be sulphided prior to carrying out the selective hydrogenation process of the invention.

The process for preparing the catalyst used in the selective hydrogenation process of the invention includes several implementations.

A first implementation consists of carrying out said steps i) and ii) simultaneously such that said organic compound, preferably a cyclodextrin, and at least said precursor of at least said metal from group VIII and at least said precursor of at least said metal from group VIB present in the active phase are co-impregnated onto said support (co-impregnation step). Said first implementation advantageously comprises carrying out one or more steps i). In particular, one or more steps i) advantageously precede and/or follow said co-impregnation step. In accordance with said first implementation, each of the (co)-impregnation steps carried out is preferably followed immediately by a step for maturation then by at least one step for drying then optionally by at least one calcining step, said calcining step preferably being carried out when the support comprises, preferably is constituted by, alumina. In particular, said co-impregnation step is followed by at least one drying step in accordance with said step iii). Said first implementation may comprise several co-impregnation steps.

A second implementation consists of carrying out said step i) prior to said step ii). In accordance with said second implementation, one or more steps i) for depositing at least said metal from group VIII and at least said metal from group VIB present in the active phase of the catalyst precede(s) said step ii). Preferably, each of said steps i) is followed immediately by a maturation step then by at least one drying step. In particular, the last step i) is advantageously followed by at least one drying step in accordance with said step iii) before carrying out said step ii). Said step ii) is advantageously followed by a maturation step then by at least one drying step which is carried out under the same conditions as those employed for said step iii), and optionally by at least one calcining step, said calcining step preferably being carried out when the support comprises, preferably is constituted by, alumina.

A third implementation consists of carrying out said step ii) prior to said step i). Said step ii) is preferably followed immediately by a maturation step then by at least one drying step and optionally by at least one calcining step before carrying out said step i). Advantageously, said step ii) is followed by several steps i). Preparation of the catalyst in accordance with said third implementation is advantageously terminated by said drying step iii), which is optionally followed by a calcining step.

Each of the three implementations described above may be carried out independently such that the catalyst used in the process of the invention is prepared either in accordance with said first implementation or in accordance with said second implementation or in accordance with said third implementation. However, it may be advantageous to associate said first implementation with said second implementation or with said third implementation: thus, both the metals from group VIII and from group VIB present in the active phase and the organic compound, preferably a cyclodextrin, are deposited on the catalyst support in at least two events, namely at least once by co-impregnation and at least once by successive impregnation.

Said drying step iii), carried out to prepare the catalyst prepared in accordance with at least one implementation described above, is carried out at a temperature in the range 80° C. to 160° C. It is preferably carried out for a period in the range 1 to 20 hours. Said step iii) is advantageously followed by at least one calcining step, in particular when the support comprises or, as is preferable, is constituted by alumina. The optional calcining step is carried out at a temperature in the range 200° C. to 550° C., preferably in the range 300° C. to 500° C. It is preferably carried out for a period in the range 1 to 6 hours.

The catalyst obtained at the end of said step iii) after carrying out steps i) and ii) in accordance with at least one of the three implementations described above is in the oxide state.

The preparation of the catalyst used in the selective hydrogenation process of the invention comprises at least one step iv) for sulphurization such that said active phase is in the sulphide form. Said step iv) is carried out after carrying out steps i), ii) and iii). It is carried out by bringing said catalyst obtained at the end of carrying out said steps i), ii) and iii) and optionally a subsequent calcining step with at least one organic sulphur-containing compound which is decomposable and a generator of $H_2S$ or by direct contact of said catalyst with a gaseous $H_2S$ stream diluted in hydrogen. Said sulphurization step iv) may be carried out in situ (i.e. after loading the catalyst into the reaction unit of the hydrodesulphurization process of the invention) or ex situ (i.e. before loading the catalyst into the reaction unit of the hydrodesulphurization process of the invention) at a temperature in the range 200° C. to 600° C. and more preferably in the range 300° C. to 500° C.

Before carrying out the hydrodesulphurization process of the invention, the catalyst from said step iv) is at least partially in the sulphide form. It may also comprise a metallic oxide phase which has not been transformed during said sulphurization step iv). Said catalyst may be entirely or partially free of said organic compound formed from at least one cyclic oligosaccharide composed of at least 6α-(1,4)-bonded glucopyranose subunits.

The following examples illustrate the invention.

EXAMPLES

Catalysts A1, A2, A3 and A4 respectively prepared in Examples 1, 2, 3 and 4 were prepared with the same contents of molybdenum, cobalt and phosphorus. The support used for the preparation of each of catalysts A1, A2, A3 and A4 was a support of alumina beads with a pore volume of 1.08 ml/g and a BET surface area of 81 $m^2$/g.

Catalysts B1, B2 and B3 respectively prepared in Examples 5, 6 and 7 were prepared with the same contents of molybdenum and cobalt. The support used for the preparation of each of catalysts B1, B2 and B3 was a support of silica extrudates with a pore volume of 0.99 ml/g and a BET surface area or 238 $m^2$/g.

Example 1 (Comparative)

Preparation of a Supported Catalyst A1 (Oxide Catalyst) and a Supported Catalyst A1' (Sulphide Catalyst) with Formula CoMoP/$Al_2O_3$ Catalyst A1 was obtained by dry impregnation of an aqueous solution prepared from molybdenum oxide, cobalt hydroxide and phosphoric acid, the volume of said solution containing the cobalt, molybdenum and phosphorus precursors being rigorously equal to the pore volume of the alumina support mass. The concentrations of the precursors in the aqueous solution were adjusted in order to deposit the desired quantities of Co, Mo and P on the alumina support. After a 12 hour maturation step, the solid was dried for 12 hours at 120° C. The solid was then calcined in air at 450° C. for 2 hours to obtain the catalyst A1.

Catalyst A1 obtained in the oxide state with formulation CoMoP had a molybdenum content of 7.6 expressed as the % by weight of the oxide $MoO_3$, a cobalt content of 1.4 expressed as the % by weight of the oxide CoO and a phosphorus content of 1.5 expressed as the % by weight of the oxide $P_2O_5$. The molar ratio Co/Mo of this catalyst was 0.35 and the molar ratio P/Mo was 0.40.

Catalyst A1 was sulphurized ex situ in the gas phase at 500° C. in a stream of $H_2S$ in hydrogen (15% by volume of $H_2S$ in $H_2$) for two hours. A catalyst A1' was obtained in the sulphide form.

Example 2 (Invention)

Preparation of a Supported Catalyst A2 (Oxide Catalyst) and a Supported Catalyst A2' (Sulphide Catalyst) with Formula CoMoP/$Al_2O_3$ in the Presence of β-Cyclodextrin (Co-Impregnation)

Catalyst A2 was obtained by dry impregnation of an aqueous solution prepared from molybdenum oxide, cobalt hydroxide and phosphoric acid, the volume of said solution containing the cobalt, molybdenum and phosphorus precursors being rigorously equal to the pore volume of the alumina support mass. The concentrations of the precursors in the aqueous solution were adjusted in order to deposit the desired quantities of Co, Mo and P on the alumina support. Said aqueous solution also contained β-cyclodextrin (SIGMA-ALDRICH, 98% pure) in a (Co+Mo)/β-cyclodextrin molar ratio of 30. After a 12 hour maturation step, the solid was dried for 12 hours at 120° C. The solid was then calcined in air at 450° C. for 2 hours to obtain the catalyst A2.

Catalyst A2 obtained in the oxide state with formulation CoMoP had a molybdenum content of 7.5 expressed as the % by weight of the oxide $MoO_3$, a cobalt content of 1.5 expressed as the % by weight of the oxide CoO and a phosphorus content of 1.5 expressed as the % by weight of the oxide $P_2O_5$. The molar ratio Co/Mo of this catalyst was 0.38 and the molar ratio P/Mo was 0.38.

Catalyst A2 was sulphurized ex situ in the gas phase at 500° C. in a stream of $H_2S$ in hydrogen (15% by volume of $H_2S$ in $H_2$) for two hours. A catalyst A2' was obtained in the sulphide form.

Example 3 (Invention)

Preparation of a Supported Catalyst A3 (Oxide Catalyst) and a Supported Catalyst A3' (Sulphide Catalyst) with Formula CoMoP/$Al_2O_3$ in the Presence of β-Cyclodextrin (Co-Impregnation of Mo, Co and P then Successive Impregnation of β-Cyclodextrin)

Catalyst A3 was obtained by dry impregnation of an aqueous solution prepared from molybdenum oxide, cobalt hydroxide and phosphoric acid, the volume of said solution containing the cobalt, molybdenum and phosphorus precursors being rigorously equal to the pore volume of the alumina support mass. The concentrations of the precursors in the aqueous solution were adjusted in order to deposit the desired quantities of Co, Mo and P on the alumina support. After a 12 hour maturation step, the solid was dried for 12 hours at 120° C. A second dry impregnation step meant that β-cyclodextrin (SIGMA-ALDRICH, 98% pure) dissolved in water could be added to the dry solid that had already been obtained. The (Co+Mo)/β-cyclodextrin molar ratio was 30. After a 12 hour maturation step, the solid was dried for 12 hours at 120° C. The solid was then calcined in air at 450° C. for 2 hours to obtain the catalyst A3.

Catalyst A3 obtained in the oxide state with formulation CoMoP had a molybdenum content of 7.5 expressed as the % by weight of the oxide $MoO_3$, a cobalt content of 1.4 expressed as the % by weight of CoO and a phosphorus content of 1.4 expressed as the % by weight of the oxide $P_2O_5$. The molar ratio Co/Mo of this catalyst was 0.36 and the molar ratio P/Mo was 0.41.

Catalyst A3 was sulphurized ex situ in the gas phase in a stream of $H_2S$ in hydrogen (15% by volume of $H_2S$ in $H_2$) for two hours at 500° C. A catalyst A3' was obtained in the sulphide form.

Example 4 (Comparative)

Preparation of a Supported Catalyst A4 (Oxide Catalyst) and a Supported Catalyst A4' (Sulphide Catalyst) with Formula CoMoP/$Al_2O_3$ in the Presence of Cellobiose (Co-Impregnation)

Cellobiose, or β-D-glucopyrannosyl(1→4)D-glucopyrannose, is the product of cellulose degradation. It is a dihoioside with empirical formula $C_{12}H_{22}O_{11}$. It is not a cyclic oligosaccharide. The developed formula of cellobiose is given below:

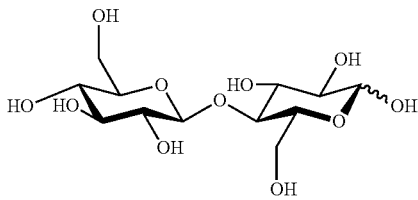

Catalyst A4 was obtained by dry impregnation of an aqueous solution prepared from molybdenum oxide, cobalt hydroxide and phosphoric acid, the volume of said solution containing the cobalt, molybdenum and phosphorus precursors being rigorously equal to the pore volume of the alumina support mass. The concentrations of the precursors in the aqueous solution were adjusted in order to deposit the desired quantities of Co, Mo and P on the alumina support. The aqueous solution also contained cellobiose (supplied by VWR) in a (Co+Mo)/cellobiose molar ratio of 30. After a 12 hour maturation step, the catalyst was dried for 12 hours at 120° C. The solid was then calcined in air at 450° C. for 2 hours to obtain the catalyst A4.

Catalyst A4 obtained in the oxide state with formulation CoMoP had a molybdenum content of 7.4 expressed as the % by weight of the oxide $MoO_3$, a cobalt content of 1.5 expressed as the % by weight of the oxide CoO and a phosphorus content of 1.5 expressed as the % by weight of the oxide $P_2O_5$. The molar ratio Co/Mo of this catalyst was 0.39 and the molar ratio P/Mo was 0.41.

Catalyst A4 was sulphurized ex situ in the gas phase in a stream of $H_2S$ in hydrogen (15% by volume of $H_2S$ in $H_2$) for two hours at 500° C. A catalyst A4' was obtained in the sulphide form.

Example 5 (Comparative)

Preparation of a Supported Catalyst B1 (Oxide Catalyst) and a Supported Catalyst B1' (Sulphide Catalyst) with Formula CoMo/$SiO_2$ Catalyst B1 was obtained by dry impregnation of an aqueous solution prepared from molybdenum oxide, cobalt carbonate and hydrogen peroxide with a $H_2O_2/MoO_3$ molar ratio of 4.5, the volume of said aqueous solution containing the precursors of the metals being rigorously equal to the pore volume of the silica support mass. The concentrations of the precursors of the Mo and Co in the aqueous solution were adjusted in order to deposit the desired quantities of Co and Mo on the silica support. After a 12 hour maturation step, the solid was dried for 12 hours at 120° C.

Catalyst B1 obtained in the oxide state with formulation CoMo had a molybdenum content of 17.8 expressed as the % by weight of the oxide $MoO_3$ and a cobalt content of 4.6 expressed as the % by weight of the oxide CoO. The molar ratio Co/Mo of this catalyst was 0.50.

Catalyst B1 was sulphurized ex situ in the gas phase at 500° C. in a stream of $H_2S$ in hydrogen (15% by volume of $H_2S$ in $H_2$) for two hours. A catalyst B1' was obtained in the sulphide form.

Example 6 (Invention)

Preparation of a Supported Catalyst B2 (Oxide Catalyst) and a Supported Catalyst B2' (Sulphide Catalyst) with Formula CoMo/$SiO_2$ in the Presence of β-Cyclodextrin (Co-Impregnation)

The catalyst was obtained by dry impregnation of an aqueous solution prepared from molybdenum oxide, cobalt carbonate and hydrogen peroxide with a $H_2O_2/MoO_3$ molar ratio of 4.5, the volume of said aqueous solution containing the precursors of the metals being rigorously equal to the pore volume of the silica support mass. The concentrations of the Mo and Co precursors in the aqueous solution were adjusted in order to deposit the desired quantities of Co and Mo on the silica support. The aqueous solution also contained β-cyclodextrin (SIGMA-ALDRICH, 98% pure) in a molar ratio (Co+Mo)/β-cyclodextrin of 30. After a 12 hour maturation step, the solid was dried for 12 hours at 120° C.

Catalyst B2 obtained in the oxide state with formulation CoMo had a molybdenum content of 17.7 expressed as the % by weight of the oxide $MoO_3$ and a cobalt content of 4.6 expressed as the % by weight of the oxide CoO. The Molar ratio Co/Mo of this catalyst was 0.50.

Catalyst B2 was sulphurized ex situ in the gas phase at 500° C. in a stream of $H_2S$ in hydrogen (15% by volume of $H_2S$ in $H_2$) for two hours. A catalyst B2' was obtained in the sulphide form.

Example 7 (Invention)

Preparation of a Supported Catalyst B3 (Oxide Catalyst) and a Supported Catalyst B3' (Sulphide Catalyst) with Formula CoMo/$SiO_2$ in the Presence of Cellobiose (Co-Impregnation)

The catalyst was obtained by dry impregnation of an aqueous solution prepared from molybdenum oxide, cobalt carbonate and hydrogen peroxide with a $H_2O_2/MoO_3$ molar ratio of 4.5, the volume of said aqueous solution containing the precursors of the metals being rigorously equal to the pore volume of the silica support mass. The concentrations of the Co and Mo precursors in the aqueous solution were adjusted in order to deposit the desired quantities of Co and Mo on the alumina support. The aqueous solution also contained cellobiose (sold by VWR) in a (Co+Mo)/cellobiose molar ratio of 30. After a 12 hour maturation step, the solid was dried for 12 hours at 120° C.

Catalyst B3 obtained in the oxide state with formulation CoMo had a molybdenum content of 17.9 expressed as the % by weight of the oxide $MoO_3$ and a cobalt content of 4.7 expressed as the % by weight of CoO. The Molar ratio Co/Mo of this catalyst was 0.50.

Catalyst B3 was sulphurized ex situ in the gas phase in a stream of $H_2S$ in hydrogen (15% by volume of $H_2S$ in $H_2$) for two hours at 500° C. A catalyst B3' was obtained in the sulphide form.

Example 8

Catalytic Performances of Catalysts A1', A2', A3', A4', B1', B2' and B3' in a Test for Hydrodesulphurization of a Gasoline Cut Using Model Molecules Representative of a Catalytically Cracked Gasoline A model feed representative of a catalytically cracked gasoline (FCC) containing 10% by weight of 2,3-dimethylbut-2-ene and 0.33% by weight of 3-methylthiophene (i.e. 1000 ppm of sulphur in the feed) was used to evaluate the catalytic performances of the various catalysts. The solvent used was heptane.

The hydrodesulphurization reaction was operated in a closed Grignard type reactor at a total pressure of 3.5 MPa at 250° C. Each of catalysts A1', A2', A3', A4', B1', B2' and B3' was placed in succession in said reactor. Samples were taken at various time intervals and were analyzed by gas chromatography to observe the disappearance of the reagents.

The catalytic performances of catalysts A1', A2', A3', A4', B1', B2' and B3' were evaluated from the catalytic activity and selectivity.

The activity of the catalyst is expressed as the rate constant kHDS of the hydrodesulphurization reaction (HDS) normalized to the volume of catalyst in the sulphide form, assuming $1^{st}$ order with respect to the sulphur-containing compounds. The selectivity of the catalyst is expressed as the normalized ratio of the rate constants kHDS/kHDO, kHDO being the rate constant for the hydrogenation reaction of olefins (HDO), namely in the present case for the hydrogenation of 2,3-dimethylbut-2-ene, normalized to the volume of catalyst in the sulphide form, assuming first order with respect to the olefins. The ratio kHDS/kHDO will be higher when the catalyst is more selective, signifying limited hydrogenation of 2,3-dimethylbut-2-ene. An increase in the ratio kHDS/kHDO is thus favourable to the quality of the gasoline obtained at the end of the hydrodesulphurization reaction, provided that olefin hydrogenation has been limited, the resulting loss of octane number of the gasoline being greatly minimized.

The performances of the catalysts supported on alumina are shown in Table 1. The values were normalized by taking catalyst A1' as the reference and taking kHDS/kHDO=100 and kHDS=100.

TABLE 1

Performances with model feed for catalysts supported on alumina

| Catalyst | kHDS | kHDS/kHDO |
|---|---|---|
| A1' (comparative) | 100 | 100 |
| A2' (invention) | 131 | 101 |
| A3' (invention) | 139 | 102 |
| A4' (comparative) | 105 | 99 |

The performances of the catalysts supported on silica are given in Table 2. The values were normalized by taking catalyst B1' as the reference and taking kHDS/kHDO=100 and kHDS=100.

TABLE 2

Performances with model feed for catalysts supported on silica

| Catalyst | kHDS | kHDS/kHDO |
|---|---|---|
| B1' (comparative) | 100 | 100 |
| B2' (invention) | 102 | 135 |
| B3' (invention) | 101 | 104 |

The results shown in Table 1 demonstrate that on alumina, adding β-cyclodextrin (catalysts A2' and A3') produces a significant gain in catalytic activity without modification to the selectivity compared with catalyst A1' prepared in the absence of β-cyclodextrin. No substantial improvement in the catalytic performances either in terms of catalytic activity or in terms of selectivity was observed when the catalyst supported on alumina was prepared in the presence of cellobiose (catalyst A4') which does not belong to the cyclic oligosaccharides family. Catalysts A2' and A3' are more active than catalysts A1' and A4'. This results in better elimination of sulphur under identical operating conditions.

The results shown in Table 2 demonstrate that on silica, adding β-cyclodextrin (catalyst B2') produces a significant gain in selectivity without deterioration of activity compared with catalyst B1' prepared in the absence of β-cyclodextrin. Adding cellobiose (catalyst B3') did not improve the catalytic performances. Thus, catalyst B2' is more selective than catalysts B1' and B3': it limits the hydrogenation of 2,3-dimethylbut-2-ene to 2,3-dimethylbutane to allow a better quality gasoline (better octane number) to be obtained than with catalysts B1' and B3'.

The invention claimed is:

1. A process for the hydrodesulphurization of a gasoline cut containing hydrocarbons containing at least 2 carbon atoms per molecule and having an end point of 250° C. or less, said process consisting of bringing said gasoline cut into contact with at least one catalyst the active phase of which comprises at least one metal from group VIII and at least one metal from group VIB deposited on a support formed from at least one oxide, said catalyst being prepared using a process comprising at least:
   i) at least one step for bringing at least said support into contact with at least one solution containing at least one precursor of at least said metal from group VIII and at least one precursor of at least said metal from group VIB;
   ii) at least one step for bringing at least said support into contact with at least one organic compound formed from at least one cyclic oligosaccharide composed of at least 6α-(1,4)-bonded glucopyranose subunits;
   iii) at least one drying step to obtain at least said metal from group VIII and at least said metal from group VIB in the oxide form; then iv) at least one sulphurization step such that said active phase is in the sulphide form;
the steps i) and ii) possibly being carried out separately, in any order, or simultaneously.

2. A hydrodesulphurization process according to claim 1, in which said gasoline cut originates from a fluid catalytic cracking unit.

3. A hydrodesulphurization process according to claim 1, in which said gasoline cut has a sulphur content in the range 200 to 5000 ppm by weight.

4. A hydrodesulphurization process according to claim 1, in which the active phase of said catalyst comprises phosphorus.

5. A hydrodesulphurization process according to claim 1, in which the metal from group VIB is molybdenum or tungsten or a mixture of said two elements.

6. A hydrodesulphurization process according to claim 1, in which the metal from group VIII is cobalt or nickel or a mixture of said two elements.

7. A hydrodesulphurization process according to claim 1, in which said support is formed from a porous solid in the oxide form selected from the group constituted by silicas, transition aluminas and silica-aluminas.

8. A hydrodesulphurization process according to claim 1, in which said organic compound is selected from cyclodextrins, substituted cyclodextrins, polymerized cyclodextrins and mixtures of cyclodextrins.

9. A hydrodesulphurization process according to claim 8, in which the cyclodextrins are α-cyclodextrin, β-cyclodextrin and ε-cyclodextrin respectively composed of 6, 7 and 8α-(1,4)-bonded glucopyranose subunits.

10. A hydrodesulphurization process according to claim 8, in which the substituted cyclodextrins are hydroxypropyl beta-cyclodextrin and methylated beta-cyclodextrins.

11. A hydrodesulphurization process according to claim 1, in which said drying step iii) is carried out at a temperature in the range 80° C. to 160° C.

12. A hydrodesulphurization process according to claim 1, in which said drying step iii) is followed by at least one calcining step.

13. A hydrodesulphurization process according to claim 1, carried out under the following operating conditions: a temperature in the range 200° C. to 400° C., a total pressure in the range 1 to 3.5 MPa with a ratio of the volume of hydrogen to the volume of gasoline cut in the range 100 to 600 liters per liter and an hourly space velocity (HSV) in the range 1 to 10 $h^{-1}$ (ratio of the volume flow rate of the liquid gasoline cut to the volume of catalyst loaded into the reactor).

14. A hydrodesulphurization process according to claim 1, in which said gasoline cut contains hydrocarbons containing at least 5 carbon atoms per molecule.

* * * * *

UNITED STATES PATENT AND TRADEMARK OFFICE
CERTIFICATE OF CORRECTION

PATENT NO. : 8,940,157 B2
APPLICATION NO. : 13/812711
DATED : January 27, 2015
INVENTOR(S) : Diehl et al.

It is certified that error appears in the above-identified patent and that said Letters Patent is hereby corrected as shown below:

In the Claims

Column 18, line 3, Claim 9 reads "and ϵ-cyclodextrin respectively composed of 6, 7 and 8α-(1," should read -- and γ-cyclodextrin respectively composed of 6, 7 and 8α-(1, --

Signed and Sealed this
Nineteenth Day of May, 2015

Michelle K. Lee
*Director of the United States Patent and Trademark Office*